(12) United States Patent
Yun et al.

(10) Patent No.: US 6,555,527 B1
(45) Date of Patent: Apr. 29, 2003

(54) HEMATOPOIETIC, MYELOPROTECTING, ANTITUMOR IMMUNE CELLS GENERATING AND RADIOSENSITIZING POLYSACCHARIDE ISOLATED FROM *PANAX GINSENG*

(75) Inventors: Yeon-Sook Yun, Kangnam-Gu (KR); Jie-Young Song, Goyang-Shi (KR); Kang-Gyu Bae, Dobong-Gu (KR); In-Sung Jung, Kuro-Gu (KR)

(73) Assignee: Korea Atomic Energy Research Institute, Taejon (KR)

( * ) Notice: Subject to any disclaimer, the term of this patent is extended or adjusted under 35 U.S.C. 154(b) by 6 days.

(21) Appl. No.: 09/641,964

(22) Filed: Aug. 21, 2000

(30) Foreign Application Priority Data

Aug. 27, 1999 (KR) .............................................. 99-35857

(51) Int. Cl.[7] ...................... A61K 31/715; A01N 43/04; C07H 1/06
(52) U.S. Cl. ......................................... 514/54; 536/128
(58) Field of Search .............................. 514/54; 536/128

(56) References Cited

U.S. PATENT DOCUMENTS 4,469,685 A * 9/1984 Kojima et al. .............. 424/195
5,071,839 A * 12/1991 Liu ............................... 514/25

FOREIGN PATENT DOCUMENTS

JP        356046817 A  *  4/1981
JP        61-18722          1/1986

* cited by examiner

Primary Examiner—James O. Wilson
Assistant Examiner—Everett White
(74) Attorney, Agent, or Firm—Oliff & Berridge, PLC

(57) ABSTRACT

The present invention relates to a polysaccharide composition having the hematopoietic, myeloprotecting, antitumor immune cell generating, and radiosensitizing activities extracted from the roots of *Panax ginseng* prepared by the steps of:

i) obtaining the residue by extracting 1 wt part of ginseng roots with 2~4 wt part of methanol;
ii) extracting and obtaining the water soluble fraction from the residue in step i) using 3~5 wt part of distilled water;
iii) freeze-drying the obtained water soluble fraction in step ii);
iv) obtaining the inner fraction using the dialysis membrane after obtaining the insoluble fraction to the 40% of ethanol from freeze-dried fraction in step iii);
v) obtaining the 6 fractions by sephacryl S-500 gel chromatography; and
vi) purifying the polysaccharide by DEAE-sephadex A-50 chromatography.

2 Claims, 15 Drawing Sheets

HEMATOPOIETIC, MYELOPROTECTING, ANTITUMOR IMMUNE CELLS GENERATING AND RADIOSENSITIZING POLYSACCHARIDE ISOLATED FROM *PANAX GINSENG*

BACKGROUND OF THE INVENTION

The present invention relates to a novel polysaccharide isolated from *Panax ginseng* having the hematopoietic, myeloprotecting, antitumor immune cells generating and radiosensitizing activities. The present invention also includes the preparation method of the polysaccharide from *Panax ginseng* and the pharmaceutical composition for enhancing the hematopoietic, myeloprotecting, antitumor immune cells generating, and radiosensitizing activities.

In detail, the polysaccharide isolated from *Panax ginseng* of the present invention is obtained by the preparation method comprising the steps of: i) obtaining the residue using methanol, ii) extracting and obtaining the water soluble fraction using distilled water, iii) obtaining the precipitate using 40% of ethanol, and iv) obtaining the polysaccharide using the dialysis membrane v) obtaining the 6 fractions by sephacryl S-500 gel chromatography vi) purification of polysaccharide by DEAE-sephadex A-50 chromatography which is composed of 6 kinds of polysaccharide being molecular weight 1,800,000~2,200,000, 1,350,000~1,650,000, 620,000~780,000, 105,000~130,000, 23,000~27,000, 5,000~6,000 dalton existing 11.4~13.4:3.6~4.2:4.5~5.1:0.7~0.9:40.1~48.1:31.0~37.0 ratio, mainly consists of $\alpha(1\to 6)$ linked D-glucopyranose units and has branches linked in part at the C-3 position.

Many polysaccharides extracted from *Panax ginseng* had been reported before the completement of the present invention. Followings are well-known reports in this regard.

Panaxan, one of glycans consisting of D-glucose, was disclosed as active ingredient for declining the blood sugar level [Konno C. et al., Isolation and hypoglycemic activity of Panaxan A.B.C.D. and E glycans of *Panax ginseng* roots, *Planta Medica* 50 pp 434~436, 1984]. The polysaccharides comprising galacturonic acid, glucose, arabinose, mannose and galactose was disclosed as the material having anti-complementary effect [Gao Q., Kiyohara H. et al., Chemical properties and anti-complementary activities of polysaccharide fractions from roots and leaves of *Panax ginseng*, *Planta Medica* 55 pp 9~12, 1989]. Further, the polysaccharide from *Panax ginseng* was reported to have antitumor or bacterial resistance activities [Japanese Laying-Open Patent No. 1986-18722 A1].

Even though such polysaccharides described above are all extracted from *Panax ginseng*, the components of such polysaccharides are different from those of the present invention. Further, polysaccharide extracted from *Panax ginseng* has never been disclosed as a material for enhancing the hematopoietic, myeloprotecting, antitumor immune cells generating and radiosensitizing activities.

On the other hand, the efficacious materials from *Panax ginseng* belong to the saponin derivatives, which have different molecular structure compared to the polysaccharide of the present invention.

β-Glucan separated from yeast cell wall has been known to have the hematopoietic activity, but has different molecular structure from the polysaccharide of the present invention. Further, the powder of OK-432, which is prepared by the heat treatment to the cell line of *Streptococcus pyrogenes* Su, together with Lentinan extracted from *Lentinus edodes*, have been disclosed as biological response modifiers (BRMs), but also have β-glucan structure.

The present invention has been completed by the purification and isolation of polysaccharide having the activities of promoting the growth of hematopoietic cells, myeloprotecting, antitumor immune cells generating, and radiosensitizing tumor cells from the roots of *Panax ginseng*.

SUMMARY OF THE INVENTION

The object of the present invention is to provide a polysaccharide composition having the hematopoietic, myeldoprotecting, antitumor immune cell generating, and radiosensitizing activities purified from the roots of *Panax ginseng* prepared by the steps of:

i) obtaining the residue by extracting 1 wt part of ginseng roots with 2~4 wt part of methanol;

ii) extracting and obtaining the water soluble fraction from the residue in step i) using 3~5 wt part of distilled water;

iii) freeze-drying the obtained water soluble fraction in step ii);

iv) obtaining the inner fraction using the dialysis membrane after obtaining the insoluble fraction to the 40% of ethanol from freeze-dried fraction in step iii);

v) obtaining 6 fractions by sephacryl S-500 gel chromatography; and vi) purifying the polysaccharide by DEAE-sephadex A-50 chromatography.

Another object of the present invention is to provide a polysaccharide which is composed of 6 kinds of polysaccharide being molecular weight 1,800,000~2,200,000, 1,350,000~1,650,000, 620,000~780,000, 105,000~130,000, 23,000~27,000, 5,000~6,000 dalton existing 11.4~13.4:3.6~4.2:4.5~5.1:0.7~0.9:40.1~48.1:31.0~37.0 ratio, consists of $\alpha(1\to 6)$ linked D-glucopyranose units with partly $\alpha(1\to 3)$ linked branches.

Also, a polysaccharide comprises more than 98.5% amount of carbohydrate and less than 1.0% amount of protein by quantitative determination.

The further object of the present invention is to provide a pharmaceutical composition having the polysaccharide for enhancing the hematopoietic, myeloprotecting, antitumor immune cells generating, and radiosensitizing activities.

DETAILED DESCRIPTION OF THE INVENTION

Figure 1:
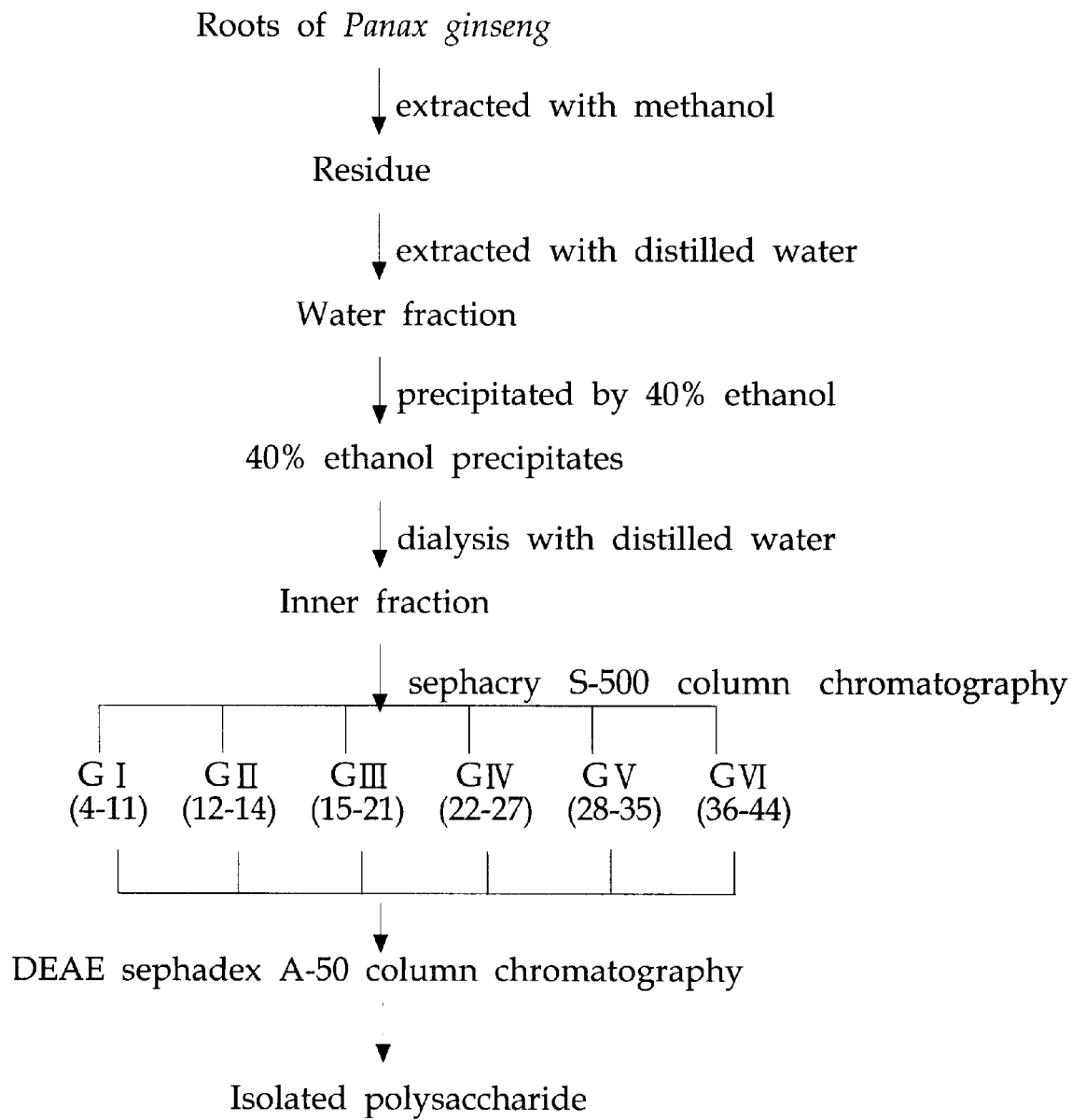
FIG. 1 shows the isolation process to obtain the polysaccharide of the present invention from *Panax ginseng*.

The isolation method of the present invention is illustrated by FIG. 1. Followings are detailed extraction process.

Figure 2:
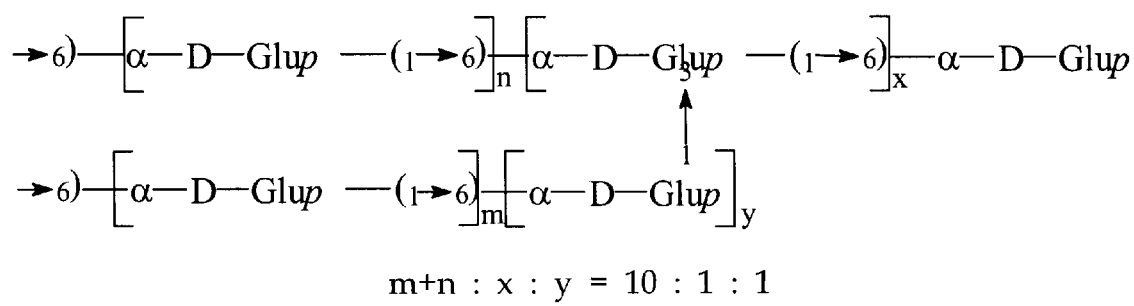
FIG. 2 shows the partial structure of the polysaccharide of the present invention from *Panax ginseng*.
Figure 3:
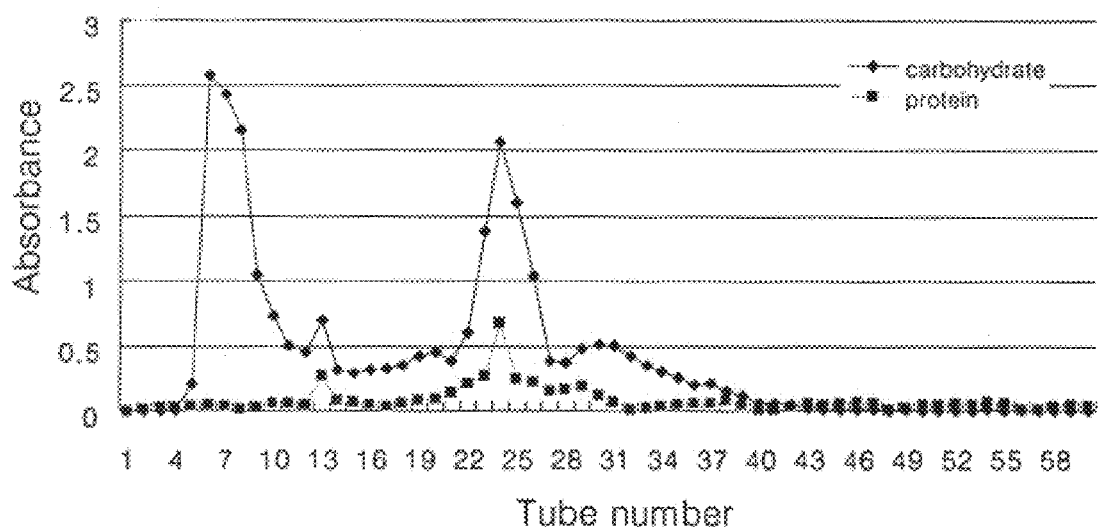
FIG. 3 shows the isolation process of the 6 kinds of polysacchaide of the present invention by sephacryl S-500 gel chromatography.

1 wt part of *Panax ginseng* was extracted with 3 wt part of methanol. After extraction, residue was obtained and dried in dark place. Then, water soluble fraction was obtained by, extraction of the residue using 4 wt part of distilled water at 4° C. for 24 hours in three times and freeze-dried. Obtained water soluble fraction is dissolved in small amount of distilled water and then precipitated by 40% of ethanol, and obtained insoluble fraction. Then, the polysaccharide fraction was obtained by dialysis using cellulose membrane against distilled water and freeze-dried. Finally, the 6 fractions of polysaccharide were obtained by sephacryl S500 gel chromatography and purified by DEAE-sephadex A-50 chromatography (FIGS. 1–3).

1) Determination of Carbohydrate Content of the Polysaccharide of the Present Invention Total carbohydrate of the polysaccharide of the present invention was determined by phenol-sulfuric acid method with D-glucose as a standard. The polysaccharide was dissolved in a concentration of 0.1 mg/ml with distilled water. Then, 30 μl of 5% phenol solution and 0.2 ml of sulfuric acid reagent was added and agitated to 20 μl of polysaccharide solution, and reacted in 60° C. for 20 minutes. Absorbance was measured at 490 nm and the carbohydrate content of polysaccharide is 98.5% compared to glucose standard.

2) Determination of Protein Content of the Polysaccharide of the Present Invention Total protein of the polysaccharide of the present invention was determined by Bradford method using Protein Assay Kit, Bio-Rad, Co. according to the manufacturer's instruction. Protein content of the polysaccharide was less than 1.0% compared to bovine serum albumin standard.

3) Identification of Sugar Components of the Polysaccharide of the Present Invention by Thin Layer Chromatography.

Figure 4:
FIG. 4 shows the TLC pattern of the polysaccharide of the present invention after acid hydrolysis.

20 mg of the polysaccharide of the present invention was reacted with 2 ml of 1M-$H_2SO_4$ at 100° C. for 4 hours, and neutralized with barium hydroxide. The polysaccharide of the present invention was consisted mainly of glucose by thin layer chromatography using a mixed solvent system of n-propanol and water(85:15, v/v) and detected with sulfuric acid. FIG. 4 shows that the polysaccharide was composed of glucose.

4) Determination of Sugar Analysis for Measuring the Components of the Polysaccharide of the Present Invention was Performed on Gas Chromatography.

20 mg of the polysaccharide of the present invention was dissolved in DMSO(2 ml) and reacted 5 minutes at 60° C. under $N_2$ gas. Methylsulfinyl carbanion(0.5 ml) was added to the polysaccharide solution and reacted at 25° C. for 1.5 hours. The reaction mixture was dialyzed with water and extracted with chloroform, the methylation was repeated until no IR absorption band for the hydroxyl group. The methylated polysaccharide was first hydrolyzed with 90% formic acid(0.5 ml) for 8 hours at 100° C., and then with 2M-trifluoroacetic acid (0.5 ml) hydrolyzed for 3 hours at 100° C. After reduction with sodium borohydride, the alditols were acetylated by heating with 0.2 ml of acetic acid-pyridine(1:1, v/v) for 2 hours at 100° C. The product was subjected to GC-Mass which was carried out under condition using a HP-5 capillary column at 280° C. The temperature condition of injector is at 280° C., and that temperature of flame ionization detector is at 300° C. Based on these results, the polysaccharide is composed of α(1→6) linked D-glucopyranose units and has branches linked in part through the 3 position; the ratio of 10:1 (Table 1).

TABLE 1

Determination of components of the polysaccharide by GC-Mass

| Derivatives | Retention time (min) | Area (%) | Main fragments (m/z) |
|---|---|---|---|
| 1,5-Ac-2,3,4,6-Me-D-Glucitol | 8.31 | 7.7 | 43, 45, 71, 88, 101, 115, 129, 145, 161, 205 |
| 1,5,6-Ac-2,3,4-Me-D-Glucitol | 9.33 | 76.9 | 43, 71, 88, 101, 115, 129, 143, 161, 186 |
| 1,3,5-Ac-2,4,6-Me-D-Glucitol | 9.44 | 7.8 | 43, 87, 101, 127, 143, 186 |
| 1,3,5,6-Ac-2,4-Me-D-Glucitol | 10.74 | 7.6 | 43, 71, 88, 101, 115, 129, 143, 161, 186 |

Ac = acetyl; Me = methyl

5) Determination of Molecular Weight of the Polysaccharide of the Present Invention Gel permeable chromatography of the polysaccharide of the present invention was performed with a Hewlett-Packard HP-600S. Mobile phase was 0.1M-sodium carbonate solution with a 1.5 ml/min flow rate and the sugars were monitored with a refractive-index detector. The molecular weight was determined by comparison of the elution time and area with standard polysaccharides, such as dextran T2000(Mw 2,000,000 dalton), T500(Mw 500,000 dalton), T70(Mw 70,000 dalton), T40(Mw 40,000 dalton) and T10 (Mw 10,000 dalton) purchased from Amersam Pharmacia Biotech. Table 2 shows that the polysaccharide of the present invention was consisted of molecular weight $1.8\sim2.2\times10^6$, $1.35\sim1.65\times10^6$, $6.2\sim7.8\times10^5$, $1.05\sim1.3\times10^5$, $2.3\sim2.7\times10^4$, $5.0\sim6.0\times10^3$ dalton being 11.4~13.4:3.6~4.2:4.5~5.1:0.7~0.9:40.1~48.1:31.0~37.0 ratio.

TABLE 2

Determination of molecular weight of the polysaccharide of the present invention by gel permeable chromatography

| Fraction | Retention time (min) | Molecular weight (dalton) | Area (%) |
|---|---|---|---|
| G I | 10.012 | $1.8\sim2.2 \times 10^6$ | 11.4~13.4 |
| G II | 10.658 | $1.35\sim1.65 \times 10^6$ | 3.6~4.2 |
| G III | 12.230 | $6.2\sim7.8 \times 10^5$ | 4.5~5.1 |
| G IV | 14.459 | $1.05\sim1.3 \times 10^5$ | 0.7~0.9 |

TABLE 2-continued

Determination of molecular weight of the polysaccharide of the present invention by gel permeable chromatography

| Fraction | Retention time (min) | Molecular weight (dalton) | Area (%) |
|---|---|---|---|
| G V | 18.693 | 2.3~2.7 × $10^4$ | 40.1~48.1 |
| G VI | 21.997 | 5.0~6.0 × $10^3$ | 31.0~37.0 |

Figure 5:
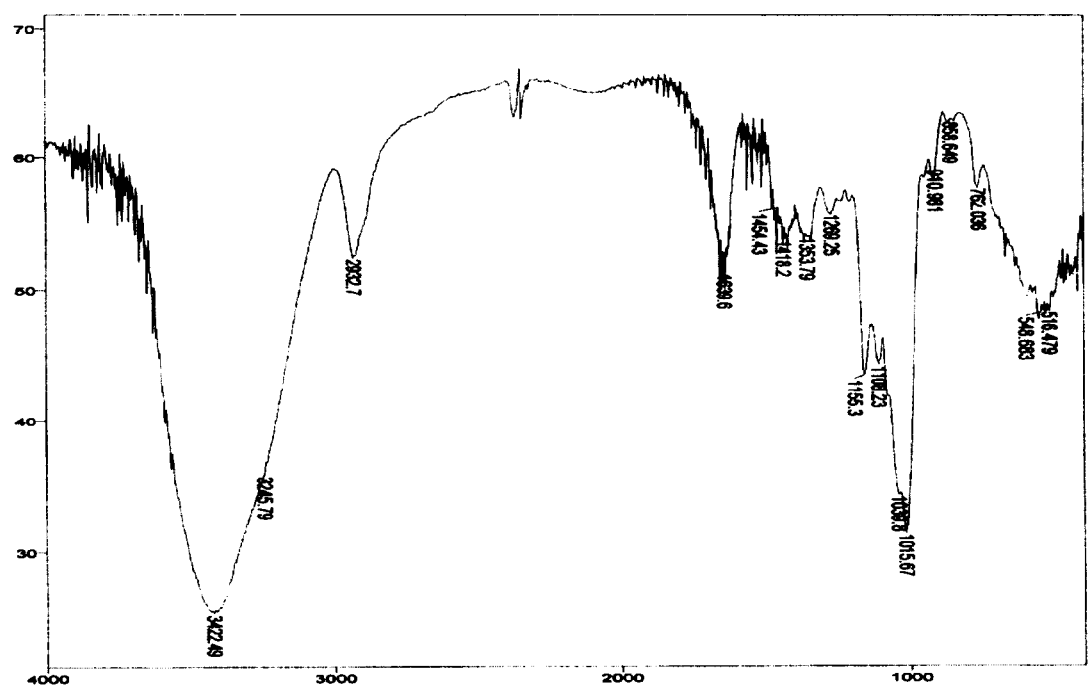
FIG. 5 shows the IR spectrum of the polysaccharide of the present invention.

6) Application of Fourier-transform Infrared(FT-IR) Spectroscopy for Characterization of the Polysaccharide of the Present Invention IR spectrum of the polysaccharide of the present invention was measured by Fourier Transform-Infra Red spectroscope, Bomem DA8.12, Hartman and Braun, Co., Canada using KBr. IR spectrum(FIG. 5) shows broad absorption band in 3400 $cm^{-1}$ indicating hydroxyl group (—OH); absorption band in 1000~1100 $cm^{-1}$ indicating ester group (C—O); and absorption band in 2800~2900 $cm^{-1}$ indicating hydrocarbons.

Figure 6:
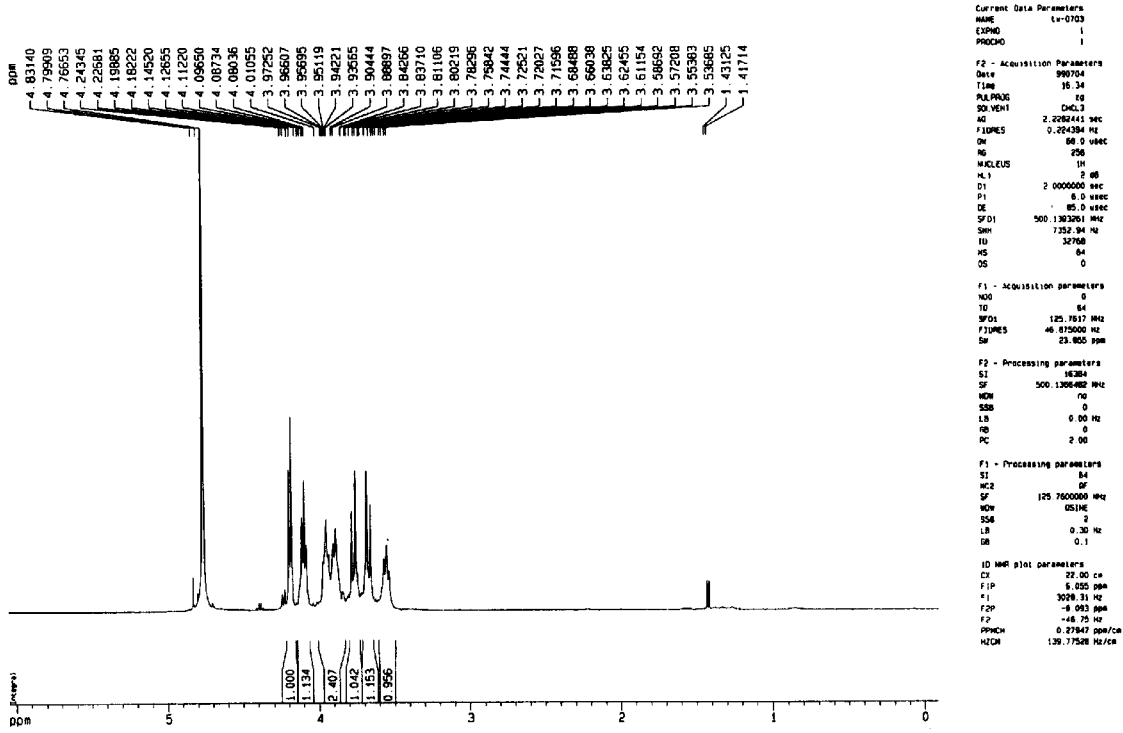
FIG. 6 shows the $^1$H-NMR spectrum of the polysaccharide of the present invention.
Figure 7:
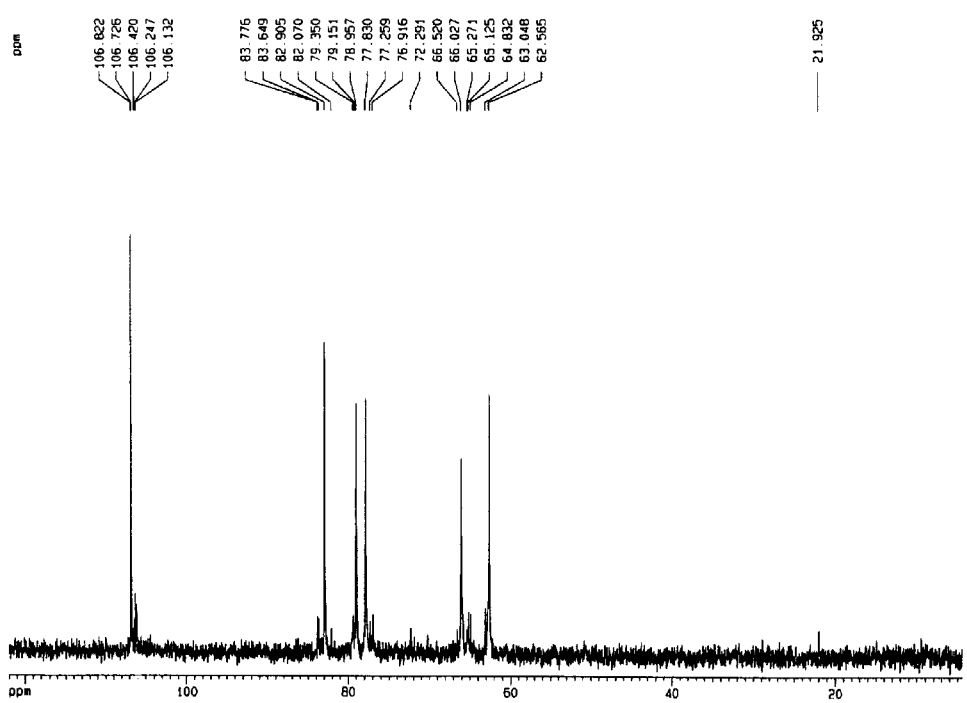
FIG. 7 shows the $^{13}$C-NMR spectrum of the polysaccharide of the present invention.

7) Application of NMR Spectroscopy for Structure Elucidation of the Polysaccharide of the Present Invention NMR spectrum of the polysaccharide of the present invention was obtained for a $D_2O$ solvent at 500 MHz Nuclear Magnetic Resonance spectroscopy, Bruker AMX 500, Germany. The proton nuclear magnetic resonance($^1$H-NMR) spectrum showed typical spectrum of glucose which exhibited at δ 3.5~4.2 due to hydroxylated methine or methylene protons, and δ 4.76(doublet, J=2.6 Hz) and 4.98 (doublet, J=3.0 Hz) due to the anomeric hydrogen proton signals(FIG. 6). The ratio of interation was being 10:1. These result suggested D-glucose units are α-linked. The $^{13}$C-NMR spectrum(FIG. 7) showed 6 major carbon signals(δ 62.6, 66.0, 77.8, 78.9, 82.8 and 106.7) and 12 minor carbon signals(δ 63.0, 64.8, 63.6, 65.1, 72.3, 76.9, 77.3, 79.2, 82.1, 83.6, 83.8, 106.1, 106.2 and 106.7). Among these signals, C-6 carbon signals absorbed at δ 62.6, 64.8 and 65.1, C-3 carbon signals absorbed at δ 82.9, 83.6 and 83.8. The C-1 carbon signals exhibited at δ 106.7, 106.1 and 106.2. These spectral properties of the polysaccharide of the present invention showed that α-D-glucose units are linked at the 1, 3 and 6 positions. This result suggested that this polysaccharide is composed of major backbone and minor branch.

Figure 8:
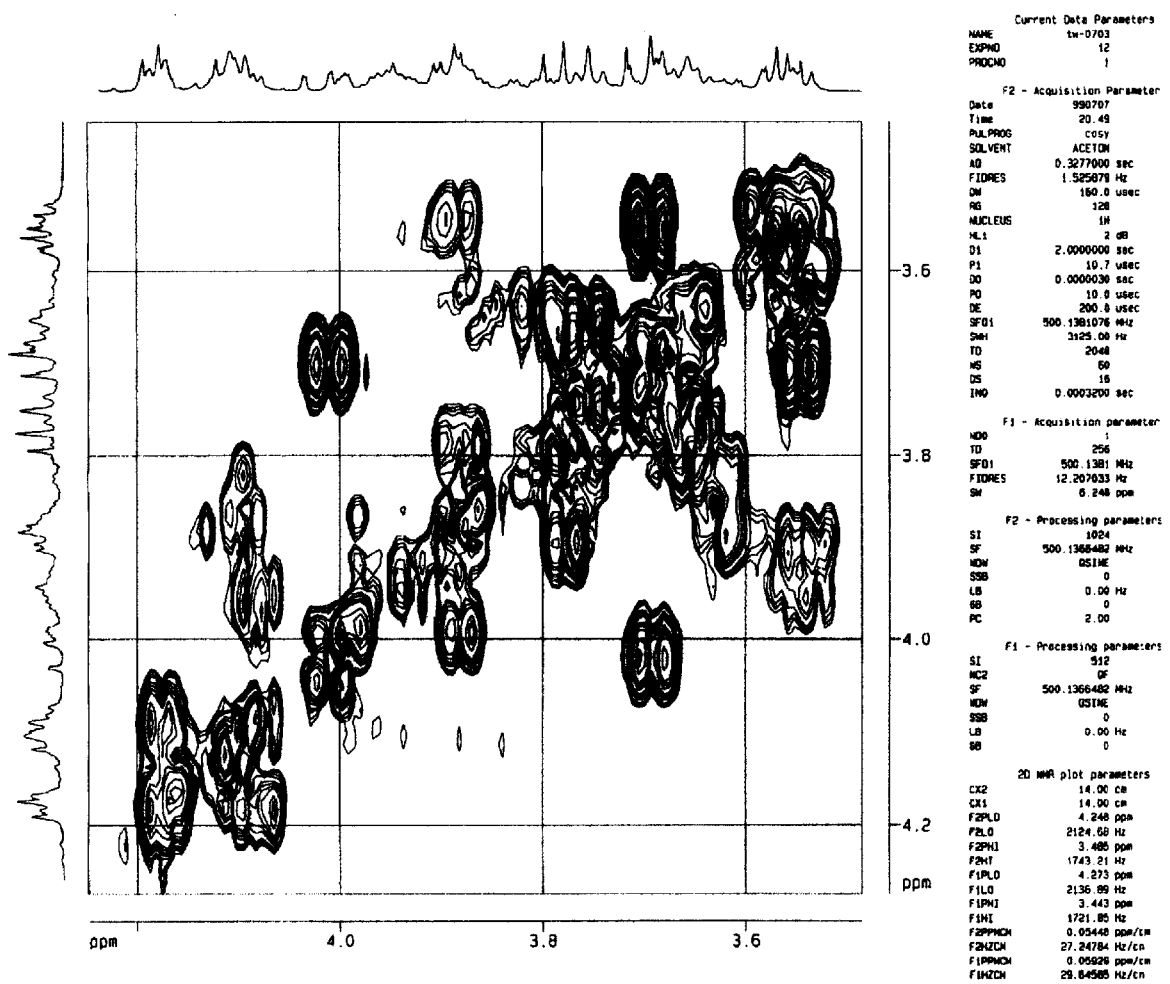
FIG. 8 shows the DQF-COSY spectrum of the polysaccharide of the present invention.
Figure 9:
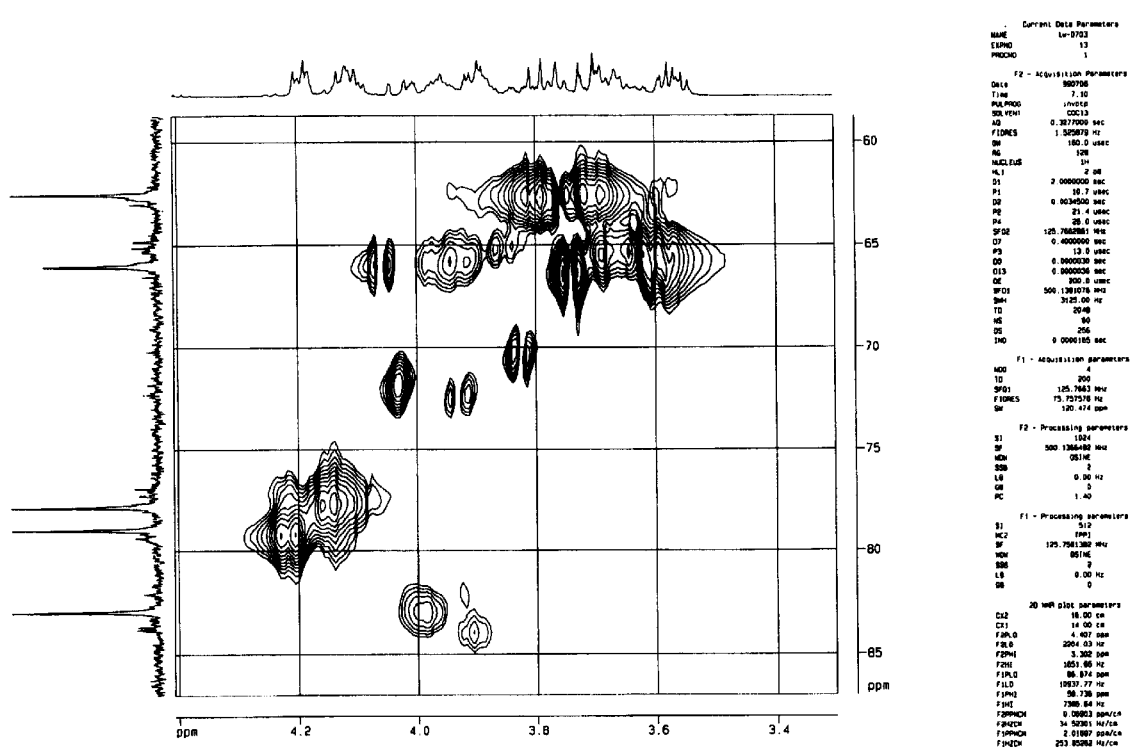
FIG. 9 shows the HMBC spectrum of the polysaccharide of the present invention.

The all of carbons and protons were matched by the Heteronuclear Multiple Quantum Correlation(HMQC) experiments. The proton and proton correlation was determined by $^1$H-$^1$H-COSY experiments(FIG. 8). The proton signal at δ 3.89 was spin coupled with δ 3.56, δ 4.10 was spin coupled with δ 4.19, δ 3.67 was spin coupled with δ 3.79 and δ 4.10, δ 3.69 was spin coupled with δ 3.79. Thus, the polysaccharide was identified to have α(1→6) glucopyranose linkage. The long-range C—H couplings were observed by Heteronuclear Multiple Bond Coherence (HMBC) experiments as shown in FIG. 9. The carbon signal at δ 66.0 showed correlation with methine proton at δ 4.10, the carbon signal at δ 82.8 showed correlation with proton at δ 3.56 and δ 4.10, the carbon signal at δ 71.8 showed correlations with protons at δ 4.19, the carbon signal at δ 78.9 showed correlations with protons at δ 3.79 and δ 4.10, the carbon signal at δ 62.6 showed correlations with protons at δ 4.19, and the carbon signals at δ 106.7 showed correlation with protons at δ 3.79, respectively. From these results, α(1→6) glucopyranose linkage was identified.

When examined the physicochemical and spectroscopic properties of present invention, the structure identified to be a α(1→6) linked D-glucopyranose units and has branches linked in part through the 3 position, the ratio of 10:1(FIG. 2).

The polysaccharide isolated from *Panax ginseng* can be used in various agents, for example, agent for promoting the growth of hematopoietic cells; agent for protecting myeloid; agent for inhibiting the suppression of hematopoietic cells induced by radio- or chemotherapy; agent for antitumor immunotherapy; agent for cancer prevention; and agent for enhancing the therapeutic efficacy of radiotherapy.

The present invention will be more specifically explained by the following example. However, it should be understood that the example is intended to illustrate but not in any manner to limit the scope of the present invention.

EXAMPLES

Example 1

Test for Promoting the Growth of Hematopoietic Cells

1) Generation of the Granulocyte Macrophage-colony Forming Unit, GM-CFU

The bone marrow cells($1\times10^5$/dish) were plated in 35 mm tissue culture dishes (with 2 mm grid, Nalge Nunc. International, Corning, N.Y., USA) containing Iscove's modified Dulbecco's medium(IMDM) supplemented with 0.3% agar, 20% horse serum and 10% recombinant GM-CSF. Polysaccharides of the present invention are treated on the according to the concentration, and the cultures were maintained at 37° C. in 5% $CO_2$ in air for 7 days. Colonies of more than 50 cells were scored. Table 3 shows that the numbers of the GM-CFU were increased from 40.67 in the control to 64.67 colonies in the cultured with ginseng polysaccharide at 50 μg/ml.

TABLE 3

Increase of the numbers of GM-CFU in the bone marrow cells by culturing with the polysaccharide of the present invention

| Treatment | Number of GM-CFU colonies ± S.D. |
|---|---|
| Bone marrow cells | 40.67 ± 4.67 |
| Bone marrow cells + Ginseng polysaccharide (100 μg/ml) | 62.33 ± 1.20 |
| Bone marrow cells + Ginseng polysaccharide (50 μg/ml) | 64.67 ± 2.91 |
| Bone marrow cells + Ginseng polysaccharide (10 μg/ml) | 54.00 ± 3.51 |

Example 2

Test for Myeloprotecting Activity

1) Property for Inhibiting the Suppression of Hematopoietic Cells Induced by Irradiation Female BALB/c mice having 18~22 g weight were put in the acryl box, and exposed to $^{60}$Co γ-irradiation at a dose rate of 97.1 cGy/min. The polysaccharide of the present invention was dissolved in phosphate buffer solution (PBS, pH 7.4), filtered using 0.45 μm Millipore membranes (Corning, N.Y.) and stored at 4° C. until the administration to the mouse. The appropriate concentrations of the polysaccharide in 0.2 ml volume were administered to normal mice by intraperitoneal injection. Control animals received 0.2 ml PBS at the same time. The blood was obtained from eyelid of mouse using the heparinized capillary tube (Chase instruments corp., Norcross, Ga.). The blood cells analysis were performed using automatic blood cell analyzer, cell-DYN 4000.

① Effect on bone marrow and spleen cellularity after irradiation

Five days after 4.5 Gy irradiation, the number of bone marrow and spleen cells in mice were measured. The number of each cells was assessed by trypan blue exclusion method.

Figure 10:
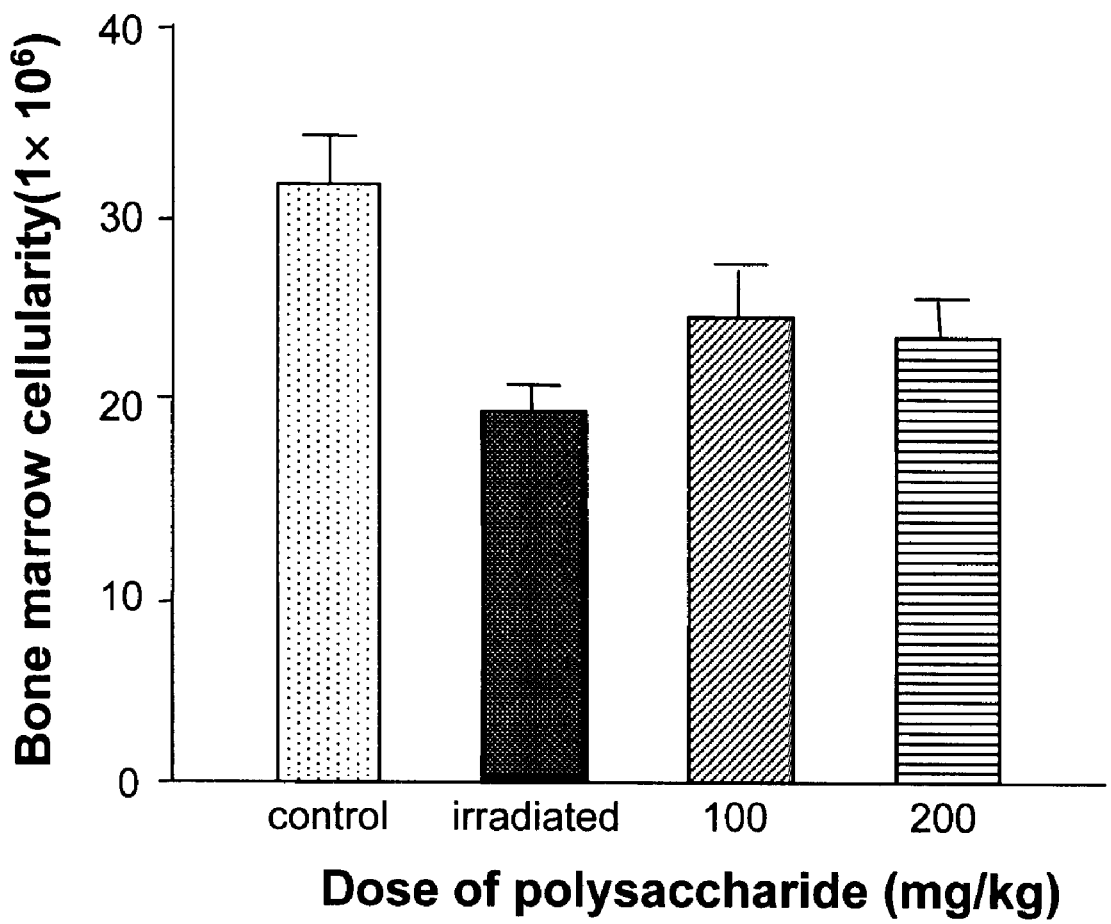
FIG. 10 shows the protecting effect on myeloid cells after $^{60}$Co γ-ray irradiation by the polysaccharide of the present invention.

The number of spleen cells and bone marrow cells in the irradiated control mice administered only PBS was less than 10% and 62% of the nonirradiated normal mice, respectively. These values increased by 1.8 fold in spleen and by 1.3 fold in bone marrow cellularity from mice injected with the polysaccharide at 100 mg/kg 24 hours before irradiation. FIG. 10 shows the results.

②  Early recovery of granulocyte macrophage-colony forming unit (GM-CFU) after sublethal irradiation.

The polysaccharide of the present invention was dissolved in PBS and administered at 100 mg/kg or 200 mg/kg by intraperitoneal injection 24 hours before irradiation. Then, the mice were irradiated at 4.5 Gy sublethal dose. The number of GM-CFU was measured on fifth day after irradiation.

Table 4 shows that the number of GM-CFU was very low in the irradiated PBS-control mice about 17% of the nonirradiated normal value, whereas the marked enhancement of GM-CFU in the polysaccharide administered group before irradiation was up to 63~80% of the normal. It shows that the polysaccharide administered group is 3.7~4.7 times early recovered compared to the control group.

TABLE 4

Effect of the polysaccharide on the number of GM-CFU in the bone marrow cells after irradiation.

| Group | Number of GM-CFU colonies ± S.D. |
| --- | --- |
| BM cells of nonirradiated normal mice | 59.33 ± 2.29 |
| BM cells of irradiated PBS control mice | 10.00 ± 1.14 |
| BM cells of irradiated polysaccharide (100 mg/kg) administered mice | 47.33 ± 3.96 |
| BM cells of irradiated polysaccharide (200 mg/kg) administered mice | 37.17 ± 2.77 |

③  Improvement effect of peripheral blood cells

Five days after 4.5 Gy sublethal irradiation, the number of white blood cells decreased from 3.463±0.236 to 0.476±0.034×10³/μL. The number of platelets decreased from 585.0±39.0 to 354.5±26.0×10³/μL and that of neutrophils and lymphcytes was also significantly decrease. As can be seen in Table 5, the hematopoietic recovery in the polysaccharide-treated mice was 2 fold faster than that of the irradiated control group, especially to the number of neutrophils.

TABLE 5

Improvement effect of the polysaccharide on hematopoietic recovery after sublethal irradiation

| | | Irradiated | | |
| --- | --- | --- | --- | --- |
| Blood cells | Non-irradiated normal ± S.D. | PBS control ± S.D. | polysaccharide (100 mg/kg) administered ± S.D. | polysaccharide (200 mg/kg) administered ± S.D. |
| Number of WBCs × 10³/μL | 3.463 ± 0.236 | 0.476 ± 0.034 | 0.948 ± 0.111 | 0.793 ± 0.055 |
| Number of neutrophils × 10³/μL | 0.367 ± 0.043 | 0.0404 ± 0.005 | 0.182 ± 0.028 | 0.271 ± 0.037 |
| Number of lymphocytes × 10³/μL | 2.975 ± 0.259 | 0.330 ± 0.041 | 0.680 ± 0.099 | 0.378 ± 0.036 |

TABLE 5-continued

Improvement effect of the polysaccharide on hematopoietic recovery after sublethal irradiation

| | | Irradiated | | |
| --- | --- | --- | --- | --- |
| Blood cells | Non-irradiated normal ± S.D. | PBS control ± S.D. | polysaccharide (100 mg/kg) administered ± S.D. | polysaccharide (200 mg/kg) administered ± S.D. |
| Number of RBCs × 10³/μL | 8.565 ± 0.121 | 7.550 ± 0.379 | 7.935 ± 0.145 | 7.663 ± 0.131 |
| Number of platelets × 10³/μL | 585.0 ± 39.0 | 354.5 ± 26.0 | 441.5 ± 38.2 | 360.1 ± 20.4 |

④  Enhancing effect of colony forming unit-spleen

Bone marrow cells were collected from the sublethal irradiated mice on fifth day (5 mice/each group) which administered PBS or the polysaccharide at 100 mg/kg 24 hours prior to irradiation. Recipient mice(10 mice/each group) received a lethal irradiation dose of 9 Gy. Bone marrow cells($10^5$) were injected intraveineously into the tail vein of the recipient mice. The number of colonies in spleens was counted microscopically 8 days later following fixation with Bouin's solution.

There is no colony to be detected in the irradiated PBS control mice, whereas mice treated with the polysaccharide at 100 mg/kg generated 17.47±2.33 CFU-S. Table 6 shows the results.

TABLE 6

Effect of the polysaccharide on CFU-S formation

| Group | CFU-S/1 × $10^5$ bone marrow ± S.D. |
| --- | --- |
| Nonirradiated normal mice | 39.25 ± 4.26 |
| Irradiated PBS control mice | None detection |
| Irradiated polysaccharide (100 mg/kg) administered mice | 17.47 ± 2.33 |

2) Inhibition Effect on the Suppression of Hematopoietic Property Induced by Anti-cancer Agent ①  Early recovery of the bone marrow, spleen cellularity and the number of GM-CFU after treatment with cyclophosphamide 50 mg/kg of the polysaccharide was administered at 24 hours after administration of 250 mg/kg cyclophosphamide. The bone marrow and spleen cells were collected from mice on ninth day, the viability of each cells was assessed by trypan blue exclusion method.

To the group administered with cyclophosphamide, the number of bone marrow cells was reduced by 76% of the normal level, but not significant statistically. In the group of the polysaccharide together with cyclophosphamide administered, there was no significant change in the number of bone marrow cells.

On the other hand, the spleen cellulatiry showed more sensitive to the treatment of cyclophosphamide. In polysaccharide(100 mg/kg) combined with cyclophosphamide administered mice, the number of spleen cell increased by 2.1 fold compared to the cyclophosphamide treated control mice which exhibited 68% of the normal value.

Further, the number of GM-CFU of the cyclophosphamide treated mice was significantly reduced by 40% of the normal level, whereas the number of GM-CFU of the polysaccharide combined with cyclophosphamide administerd mice increased by 1.94 times more than the cyclophosphamide treated control mice. Table 7 shows the results.

TABLE 7

Enhancement of the number of bone marrow, spleen cells and GM-CFU by the polysaccharide combined with cyclophosphamide

| Group | Test | | |
|---|---|---|---|
| | Number of bone marrow cells ($\times 10^6$) ± S.D. | Number of spleen cells ($\times 10^7$) ± S.D. | Number of colonies of GM-CFU ± S.D. |
| Nontreated normal mice | 30.72 ± 1.39 | 17.53 ± 0.77 | 46.50 ± 6.31 |
| Cyclophosphamide treated control mice | 23.36 ± 1.61 | 11.99 ± 2.35 | 19.25 ± 1.93 |
| Cyclophosphamide and polysaccharide treated mice | 25.66 ± 2.37 | 25.65 ± 1.55 | 37.25 ± 4.57 |

Example 3

Test for Activation of Antitumor Immune Cells
1) Test for Activation of Natural Killer (NK) Cells C3H/HeN mouse was housed five mice and administered PBS or polysaccharide at 10, 50, 100, 200 mg/kg by intraperitoneal injection. Four hour [$^{51}$Cr] release assay was used to determine the generation of natural killer cells. Briefly, Spleen cells($1.5 \times 10^6$ cell/ml) were prepared at 24 hours after the polysaccharide administration and cultured with [$^{51}$Cr]-labeled target cells, YAC-1(effector cell:target cell=100:1) for 4 hours in 96 well-U-bottomed microplates. The plate were harvested and radioactivity released in the supernatants was determined by using γ-counter (Beckmann Inst., Palo Alto., Calif., USA). The percentage of specific release was calculated as: % of specific release=(ER-SR)/(MR-SR)×100, where ER is the mean count from the experimental group, SR is the mean count from target cells incubated in medium alone, MR is the mean count from target cells treated with 0.5% triton X-100. The polysaccharide at 100 mg/kg treated group exhibited 42.4% cytotoxicity to YAC-1 tumor cell, which is 3.5 times higher than 12.1% of the control. Table 8 shows the results.

TABLE 8

Test for activating of natural killer (NK) cells

| Group | % cytotoxicity at E:T = 100:1 (mean ± S.D.) |
|---|---|
| Control group | 12.1 ± 0.2 |
| Polysaccharide(10 mg/kg) administered | 18.4 ± 2.4 |
| Polysaccharide(50 mg/kg) administered | 25.3 ± 0.5 |
| Polysaccharide(100 mg/kg) administered | 42.4 ± 3.6 |
| Polysaccharide(200 mg/kg) administered | 12.4 ± 1.2 |

2) Test for Activation of Cytotoxic T Lymphocytes

The MOPC 315 plasmacytoma cell line (American Type Culture Collection, Rockville, Md.) was cultured in Dulbecco's modified Eagles medium (DMEM) containing penicillin, streptomycin and 10% fetal calf serum (FCS). MOPC 315 cells at $1 \times 10^6$ were injected subcutaneously (s.c.) into Balb/c mice. After 3 days later, the polysaccharide was administered to mice at concentrations of 50, 10, 2 mg/kg every other day by intraperitoneally injections for 4 times. After 14 days, spleen cells were harvested, and the CTL activity was assayed against $^{51}$Cr-labeled target cells. Variable numbers of effector cells were mixed with $10^4$ $_{51}$Cr-labeled MOPC315 tumor cells in triplicate and cultured in 96-well U-bottomed tissue culture plates. After 4 hours the plates were centrifuged at 400 g for 5 min, and 0.1 ml supernatant was collected and counted in a gamma counter. The polysaccharide at 2, 10, 50 mg/kg administered group exhibited 18.6, 22.4, 17.8% cytotoxicity to MOPC 315 cell, respectively. Table 9 shows the results.

TABLE 9

Test for activation of cytotoxic T lymphocytes (CTL) by the polysaccharide

| Group | % cytotoxicity at E:T = 100:1 (mean ± S.D.) |
|---|---|
| Control mice | 0.9 ± 0.2 |
| Polysaccharide(2 mg/kg) administered mice | 18.6 ± 1.0 |
| Polysaccharide(10 mg/kg) administered mice | 22.4 ± 1.6 |
| Polysaccharide(50 mg/kg) administered mice | 17.8 ± 1.2 |

3) Test for Tumoricidal Activity of the Peritoneal Macrophage Cultured with the Polysaccharide.

Peritoneal macrophages of C3H/HeN mice were isolated and seeded $2 \times 10^5$ cells/well in 96 well-U-bottomed microplates with or without the polysaccharide for 24 hours at 37° C., 5% $CO_2$ incubator. The peritoneal macrophages were washed with PBS to remove polysaccharide and incubated with YAC-1 cells at $1 \times 10^4$ cells/well in the presence of 2 μCi/well of $^3$H-thymidine. After 24 hours, the cells were harvested using an automatic multiwell harvester and the amount of radioactivity incorporated in the target cells were counted in a liquid scintillation counter. The peritoneal macrophages cultured with 10, 50, 100 μg/ml of polysaccharide inhibited the growth of YAC-1 cancer cells by 52.6, 69.2, 59.8%, respectively. Table 10 shows the results.

TABLE 10

Tumoricidal activity of the macrophages cultured with the polysaccharide

| Treatment | % inhibition |
|---|---|
| Peritoneal macrophage (PM) | 15.9 ± 4.1 |
| PM + polysaccharide(10 μg/ml) | 59.8 ± 6.9 |
| PM + polysaccharide(50 μg/ml) | 69.2 ± 2.6 |
| PM + polysaccharide(100 μg/ml) | 52.6 ± 5.0 |

4) Test for Antitumorigenecity in vivo.

Figure 11:
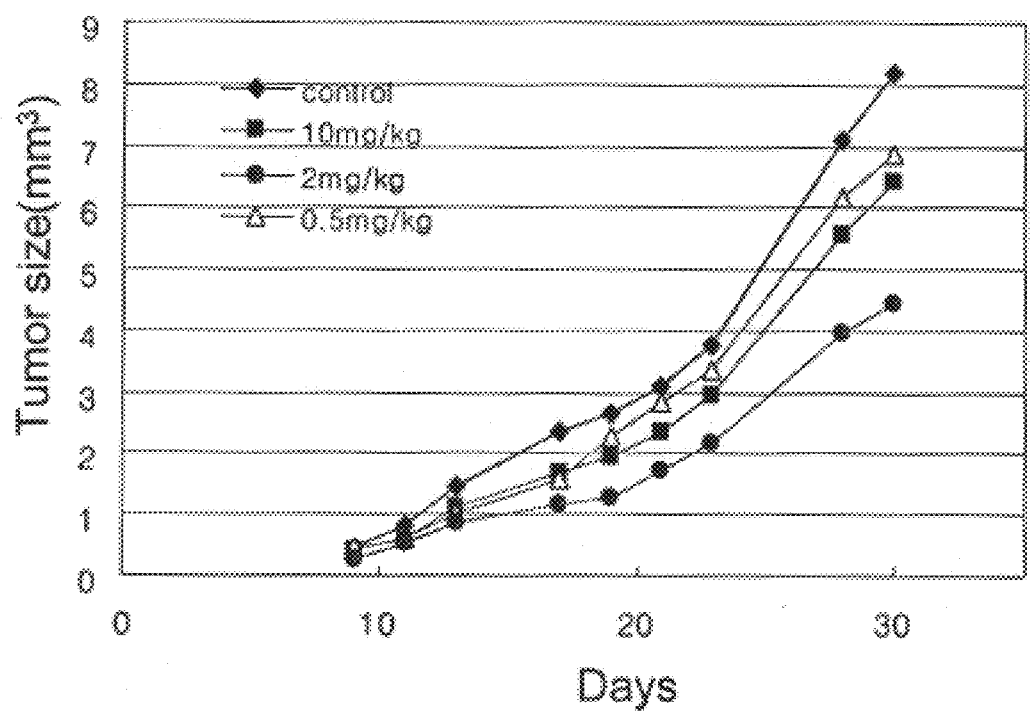
FIG. 11 shows the anti-tumor effect by the polysaccharide of the present invention in vivo.

MOPC 315 tumor cells ($1 \times 10^6$ cells/mice) were injected s.c. into Balb/c mice. 10, 2, 0.5 mg/kg of polysaccharide and PBS were intraperitoneally injected 8 times every other day from 3 days after tumor implantation. FIG. 11 shows that 10, 2, 0.5 mg/kg of the polysaccharide administered mice were reduced by 22%, 46%, 16% of tumor size compared with the control mice at 30 days.

5) Test for Cancer Prophylactic Effect

Balb/c mice were divided into four groups and each group contained 50 mice. 0.5 mg benzo[α]pyrene in 1% aqueous gelatin was subcutaneously injected in the scapular region within 24 hours after birth and the polysacchride dissolved at 0.5, 2, 10 mg/mg in drinking water was administered for 9 weeks after weaning ad libitum. The mice were sacrificed and the lung were removed, and then fixed in Bouin's solution. The numbers of the nodules in lungs were counted under microscope. As can be seen in Table 11, the incidence of lung tumor in BP alone group was 62%, it was significantly decreased by the treatment with polysaccharide by 31%, 23% and 45%, respectively.

TABLE 11

Inhibition of tumor incidence by the polysacchride

| Group | % incidence of lung tumor |
|---|---|
| Benzo[α]pyrene(BP) | 60 |
| BP + polysaccharide(0.5 mg/ml) | 30 |
| BP + polysaccharide (2 mg/ml) | 22 |
| BP + polysaccharide (10 mg/ml) | 44 |

6) Test for Cytokine mRNA Expression

Figure 12:
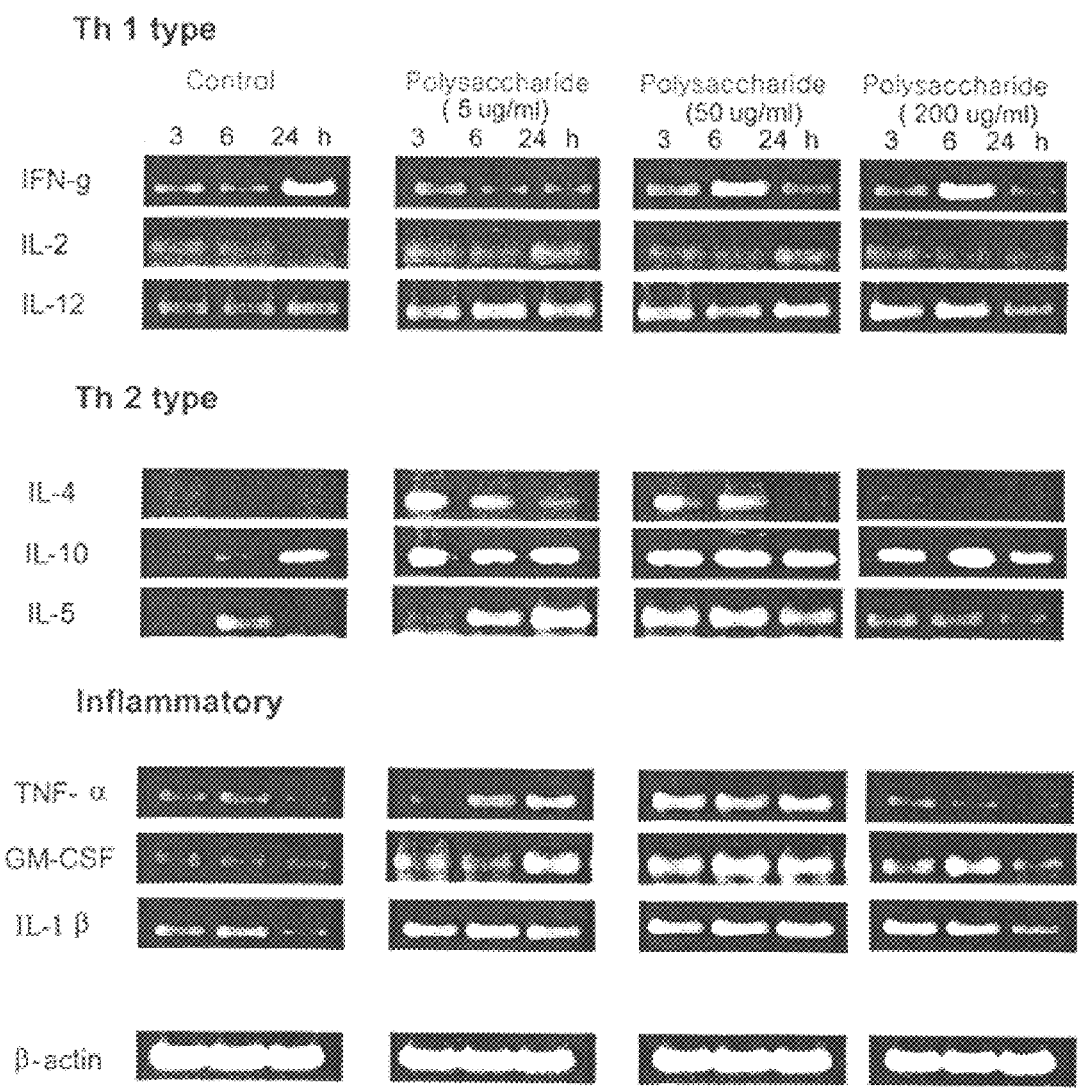
FIG. 12 shows the effect for enhancing the cytokine expression mRNA by the polysaccharide of the present invention.

Spleen cells ($2 \times 10^6$ cells/ml) of C3H/HeN mice were seeded to 6 well plate with various concentration of the polysaccharide (5 μg/ml, 50 μg/ml, 200 μg/ml), and incubated for 1, 3, 6, 24 hours. After incubation, the cells were washed and total RNA was isolated. One microgram of total RNA was reverse transcribed at 37° C. for 60 min. The reverse transcriptase was inactivated at 95° C. for 5 minutes and cDNA was amplified by the polymerase chain reaction (PCR) under the condition of 2.5 U of the Taq polymerase, 10 μM of dNTPs each, 40 pmol of the cytokine primers, and 1.5 mM of magnesium chloride. The PCR product was electrophoresed on 2% agarose gel stained with ethidium bromide and compared with DNA size marker, λDNA-BstEII Digest. Each cytokine mRNA expression was quantitated using an image analyzer with MCID software program compared with β-actin. The expression of IL-2, IFNγ, IL-12 mRNA from Th1 cells; IL4, IL-5, IL-10 from Th2 cells and TNFα, GM-CSF, IL-1β from macrophages were induced. FIG. 12 shows the results.

Example 4

Test for Enhancing Effect on the Radiosensitivity of Tumor Cells

1) Test for Generation of Nitric Oxide

Figure 13:
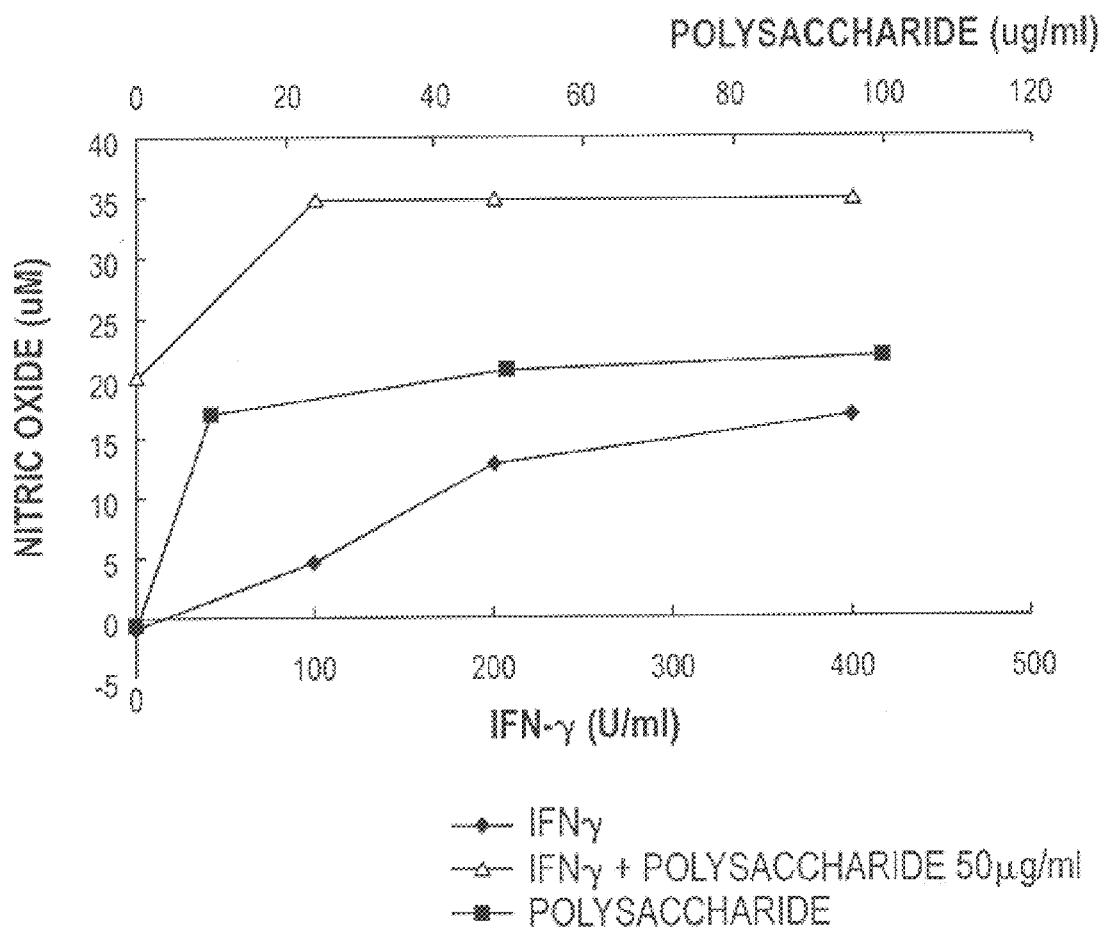
FIG. 13 shows the effect for generation of nitric oxide in cancer cell line by the polysaccharide of the present invention.

Because the radiosensitizing effect of NO is well documented, we estimated NO production and radiosensitizing effect of polysaccharide in Line1 cell lines. The accumulation of $NO_2^-$, a stable end product of NO formation, in tumor cell culture supernatants was used as a relative measurement of NO production. Cells were seeded onto 96 well plate at $5 \times 10^4$ cells/well with the polysaccharide (100 μg/ml) or IFN-γ(50 U/ml). After 24 hours incubation, 100 μl of cell-free supernatant were incubated with 100 μl of Griess reagent (0.1% naphthylethylene diamine dihydrochloride in $H_2O:0:1\%$ sulfanilamide in 5% $H_3PO_4=1:1$) for 10 min at room temperature, and the absorbance at 550 nm was measured using microplate reader. The concentration of $NO_2^-$ was determined from a least squares linear regression analysis of a sodium nitrite standard that was generated with each experiments. As shown in FIG. 13, cells treated with the polysaccharide (100 μg/ml) produced 21.6 μM of $NO_2^-$, and IFNγ produced 16.7 μM of $NO_2^-$. When cells were treated by polysaccharide (100 μg/ml) combined with IFNγ(50 U/ml), there was a synergistic effect.

2) Estimation of Radiosensitizing Effect

Figure 14:
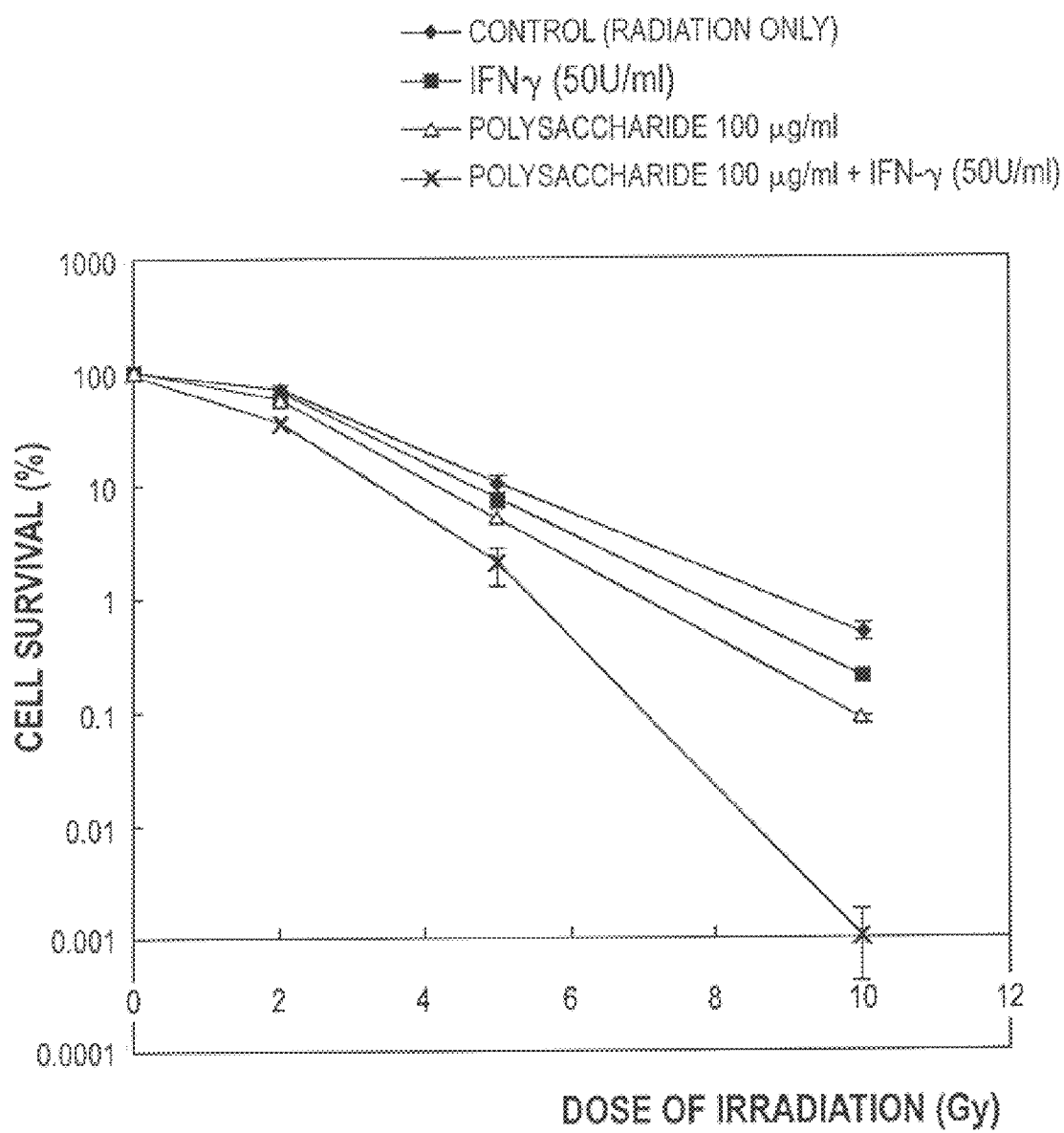
FIG. 14 shows the radiosensitizing activity in cancer cell line by the polysaccharide of the present invention.

Line1 cells in log-phase growth were harvested and seeded onto 6 $mm^2$ culture dishes with the polysaccharide, IFN-γ or the polysaccharide combined with IFN-γ during 16 hours, and irradiated. The number of cells per dish was manipulated so that 50–200 colonies survived at each condition. After 7 days incubation, colonies were stained with 1% methylene blue in absolute methanol, and counted. Colonies containing >50 cells were scored. Enhancement Ratio (ER) is calculated by dividing the radiation dose for the control conditions by the radiation dose for the various agents treated conditions at the 1% surviving fraction level. FIG. 14 shows the radiation survival curves for Line 1 cells treated with the polysaccharide (100 μg/ml) and IFN-γ(50 U/ml). The ERs for the polysaccharide was 1.28, for IFN-γ was 1.14. The ER of the combination effect of the polysaccharide and IFN-γ was 1.66.

3) Test for Radiosensitizing Effect in vivo

Figure 15:
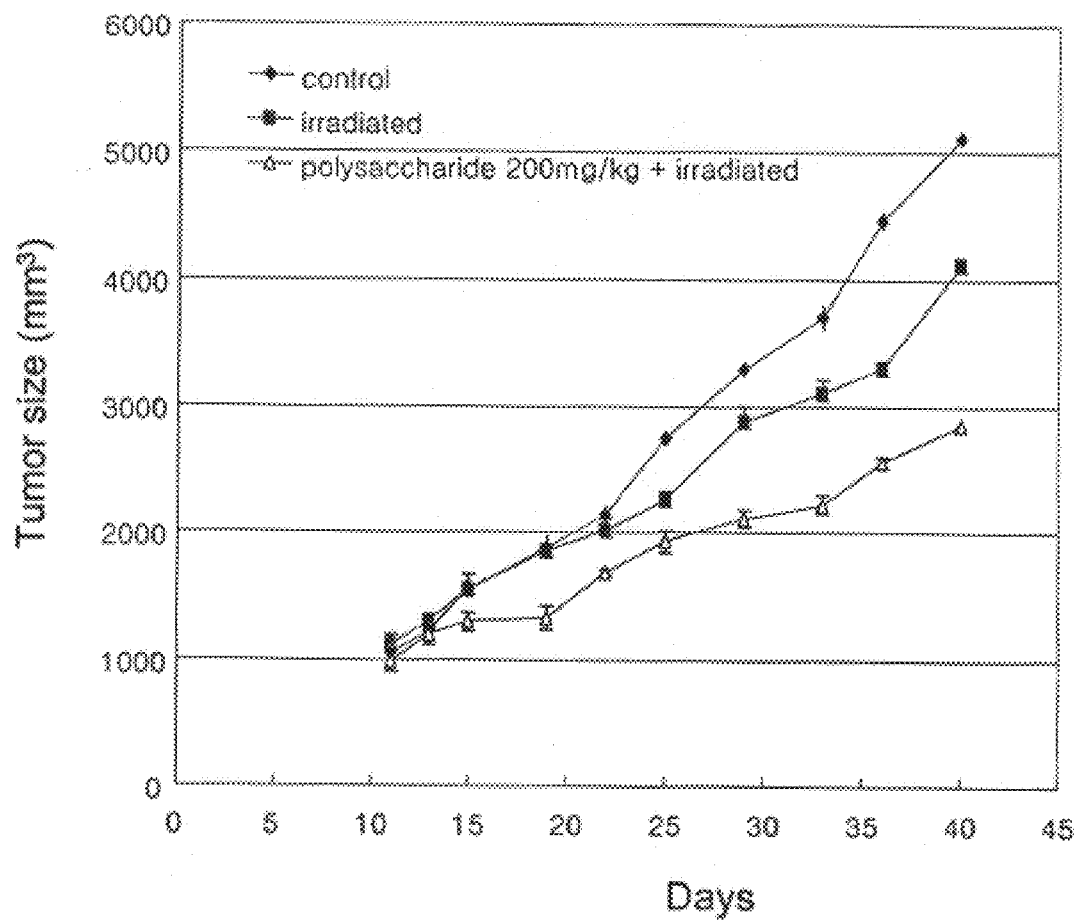
FIG. 15 shows the enhancing effect on the radiotherapeutic efficacy by the polysaccharide of the present invention.

To investigate radiosensitizing effect of the polysaccharide in vivo, Line 1 cells were transplanted in Balb/c female mice. Treatments were initiated once the tumors had reached a mean volume of 1000 $mm^3$. Tumor volume was determined by direct measurement with calipers and calculated by the formula (length×width×depth/2) and reported as the mean volume±S.E. Mice were injected with PBS or the polysaccharide (200 mg/kg) intraperitoneally 3 times every other day. After treatment, mice were subjected 20 Gy radiation at dose rate 65,8 cGy/min. When the polysaccharide administration and radiation were combined, the tumors actually regressed by 45% of the control mice in the same time period (FIG. 15).

Example 5

Test for Acute Toxicity

To measure acute toxicity of the polysaccharide, 2 g/kg, 1 g/kg, 200 mg/kg or 40 mg/kg of the polysaccharide was intraperitoneally injected. The number of deaths occurring over the 30-day period was scored. Table 12 shows the results.

TABLE 12

| | Test of acute toxicity | | | |
|---|---|---|---|---|
| Dosage of polysaccharide | 2 g/kg | 1 g/kg | 200 mg/kg | 40 mg/kg |
| Number of dead mice | 0 | 0 | 0 | 0 |

The polysaccharide of the present invention can be prepared to pharmaceutical preparation using conventional carriers. The formulation can be used in various ways, for example, tablet, dispersant, granule, capsule, solution or injection in oral or none-oral dosage form.

The dosage of the polysaccharide can be varied according to the status of patient, weight, age and sex. Generally, 100~1,000 mg/day/60 kg is preferred.

What is claimed is:

1. A polysaccharide composition having hematopoietic, myeloprotecting, antitumor immune cell generating, and radiosensitizing activities extracted from the roots of *Panax ginseng* comprising 6 fractions of polysaccharide having molecular weights of 1,800,000~2,200,000, 1,350,000~1,650,000, 620,000~780,000, 105,000~130,000, 23,000~27,000, 5,000~6,000 dalton, with weight ratios of 11.4~13.4:3.6~4.2:4.5~5.1:0.7~0.9:40.1~48.1:31.0~37.0, respectively, consisting of α(1→6) linked D-glucopyranose units with partly α(1→3) linked branches, wherein said 6 fractions of polysaccharide are prepared by the steps of:
  i) obtaining a residue by extracting 1 wt part of ginseng root with 2~4 wt part of methanol;
  ii) extracting and obtaining a water soluble fraction from the residue in step i) using 3~5 wt part of distilled water;
  iii) freeze-drying the obtained water soluble fraction in step ii);
  iv) obtaining an inner fraction using the dialysis membrane after obtaining an insoluble fraction from the freeze-dried fraction in step iii);
  v) obtaining the 6 fractions by sephacryl S-500 gel chromatography; and
  vi) passing the polysaccharide composition obtained in step v) through DEAE-sephadex A-50 chromatography,
  and said 6 fractions of polysaccharide comprises more than 98.5% amount of carbohydrates moiety and less than 1.0% amount of proteins moiety by quantitative determination.

2. A pharmaceutical composition having the efficacious amount of the polysaccharide composition of claim 1 for hematopoietic agents, myeloprotector, inhibitor of radiation and/or anticancer agents induced hazard, chemoprevention agents and radiosensitizer.

* * * * *

UNITED STATES PATENT AND TRADEMARK OFFICE
CERTIFICATE OF CORRECTION

PATENT NO. : 6,555,527 B1 Page 1 of 1
DATED : April 29, 2003
INVENTOR(S) : Yeon-Sook Yun et al.

It is certified that error appears in the above-identified patent and that said Letters Patent is hereby corrected as shown below:

<u>Title page,</u>
Item [75], Inventors, should read as follows:
-- Yeon-Sook Yun, Seoul (KR);
Jie-Young Song, Goyang-Shi (KR);
Kang-Gyu Bae, Seoul (KR);
In-Sung Jung, Seoul (KR) --

Signed and Sealed this

Sixteenth Day of September, 2003

JAMES E. ROGAN
*Director of the United States Patent and Trademark Office*